US007846191B2

United States Patent
Vaynberg et al.

(10) Patent No.: US 7,846,191 B2
(45) Date of Patent: Dec. 7, 2010

(54) METHOD AND SYSTEM FOR CONTROLLING NON-COHERENT PULSED LIGHT

(75) Inventors: Boris Vaynberg, Zichron Ya'akov (IL); Haim Epshtein, Benyamina (IL); Shimon Panfil, Haifa (IL); Yoni Iger, Haifa (IL)

(73) Assignee: Lumenis Ltd., Yokneam (IL)

( * ) Notice: Subject to any disclaimer, the term of this patent is extended or adjusted under 35 U.S.C. 154(b) by 1534 days.

(21) Appl. No.: 10/916,637

(22) Filed: Aug. 12, 2004

(65) Prior Publication Data

US 2005/0107850 A1    May 19, 2005

Related U.S. Application Data

(60) Provisional application No. 60/494,098, filed on Aug. 12, 2003.

(51) Int. Cl.
*A61N 5/06* (2006.01)
(52) U.S. Cl. .............................. 607/88; 607/90; 606/9; 606/10; 606/12
(58) Field of Classification Search ............. 607/88–91, 607/96, 100; 606/8–12; 128/898
See application file for complete search history.

(56) References Cited

U.S. PATENT DOCUMENTS

| 4,076,421 | A |   | 2/1978 | Kishner |           |
|-----------|---|---|--------|---------|-----------|
| 5,720,772 | A | * | 2/1998 | Eckhouse | .......... 607/88 |
| 5,725,522 | A | * | 3/1998 | Sinofsky | .......... 606/8 |

OTHER PUBLICATIONS

International Search Report for PCT/IL04/00742 mailed Feb. 1, 2006.
European Search Report, Application No. 04745081.2, dated Apr. 12, 2007.

* cited by examiner

*Primary Examiner*—Ahmed M Farah
(74) *Attorney, Agent, or Firm*—Mintz Levin Cohn Ferris Glovsky and Popeo, P.C.

(57) ABSTRACT

A system and method to control non-coherent pulsed light, the system including a lamp to produce non-coherent light energy in a pulsed mode, a current supply to provide energy to the system, and a switching module to control the spectral distribution and/or light intensity in the non-coherent pulsed light energy during a pulse of non-coherent light. The system may include a controller unit to control pulse parameters for a selected treatment, based on illumination data received from the light sensor. The system may include one or more changeable filters to modulate the pulses supplied to the lamp during a pulse.

8 Claims, 7 Drawing Sheets

METHOD AND SYSTEM FOR CONTROLLING NON-COHERENT PULSED LIGHT

CROSS REFERENCE TO RELATED APPLICATIONS

This application claims priority from U.S. Provisional Patent Application No. 60/494,098, filed Aug. 12, 2003, entitled "METHOD AND SYSTEM FOR CONTROLLING NON-COHERENT PULSED LIGHT", which is incorporated in its entirety herein by reference.

FIELD OF THE INVENTION

The present invention relates to methods and devices useful in providing non-coherent pulsed light. Specifically, embodiments of the present invention relate to systems and apparatuses that enable controlling the delivery of non-coherent pulsed light.

BACKGROUND

Light therapy generally involves applying light energy to increase the local temperature at a target location in a body, as a result of the absorption of photons distributed in the target tissue. The photon distribution, and therefore local temperature rise, is generally determined by the features of the light source and physical properties of the medium used for conveying the light to a target. Selective Photothermolysis Theory (SPT), which may be a physical foundation for many light treatments, typically involves choosing parameters of the therapeutic light being used, for example, wavelength, pulse magnitude and pulse duration, etc., in such way that the temperature rise is sufficiently large to incur required effects in a target, yet remain below a safety threshold in the surrounding tissues.

SUMMARY OF THE INVENTION

There is provided, in accordance with an embodiment of the present invention, a system to control non-coherent pulsed light, the system including a lamp to produce non-coherent light energy in a pulsed mode, a power supply to provide energy to the system, a capacitor to generate current in the lamp; and a current modulator to modulate energy flow between the power supply and the lamp. The system may include a controller unit to control pulse parameters for a selected treatment, based on illumination data received from the light sensor. The system may include a switching module to modulate power supplied to the lamp during a pulse. The system may include one or more changeable filters to modulate the pulses supplied to the lamp during a pulse.

According to some embodiments of the present invention, a method to control non-coherent pulsed light may include generating a pulse to provide treatment to a selected target according to a treatment plan, sensing the light output from the target, processing sensed signals to determine if the light output complies with predetermined pulse parameters and/or biological characteristics, and if the predetermined pulse parameters and/or biological characteristics are not being met, controlling the spectral distribution and/or the light intensity of the light output during a pulse.

According to some embodiments of the present invention, treatments with multiple modes of operation within a pulse may be implemented, to enable differentiation between target and surrounding tissue. Such treatments may help improve the safety and/or efficacy of treatments of targets located in dark skin types, of targets having physical properties similar to or only slightly different from surrounding tissue, of targets located deep in the dermis, and/or any combinations of the above treatments. Furthermore, treatment for hair removal, blood vessel modification, textural lesions and/or other procedures may be aided using treatments with multiple modes of operation within a pulse, as described above.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

Figure 1A:
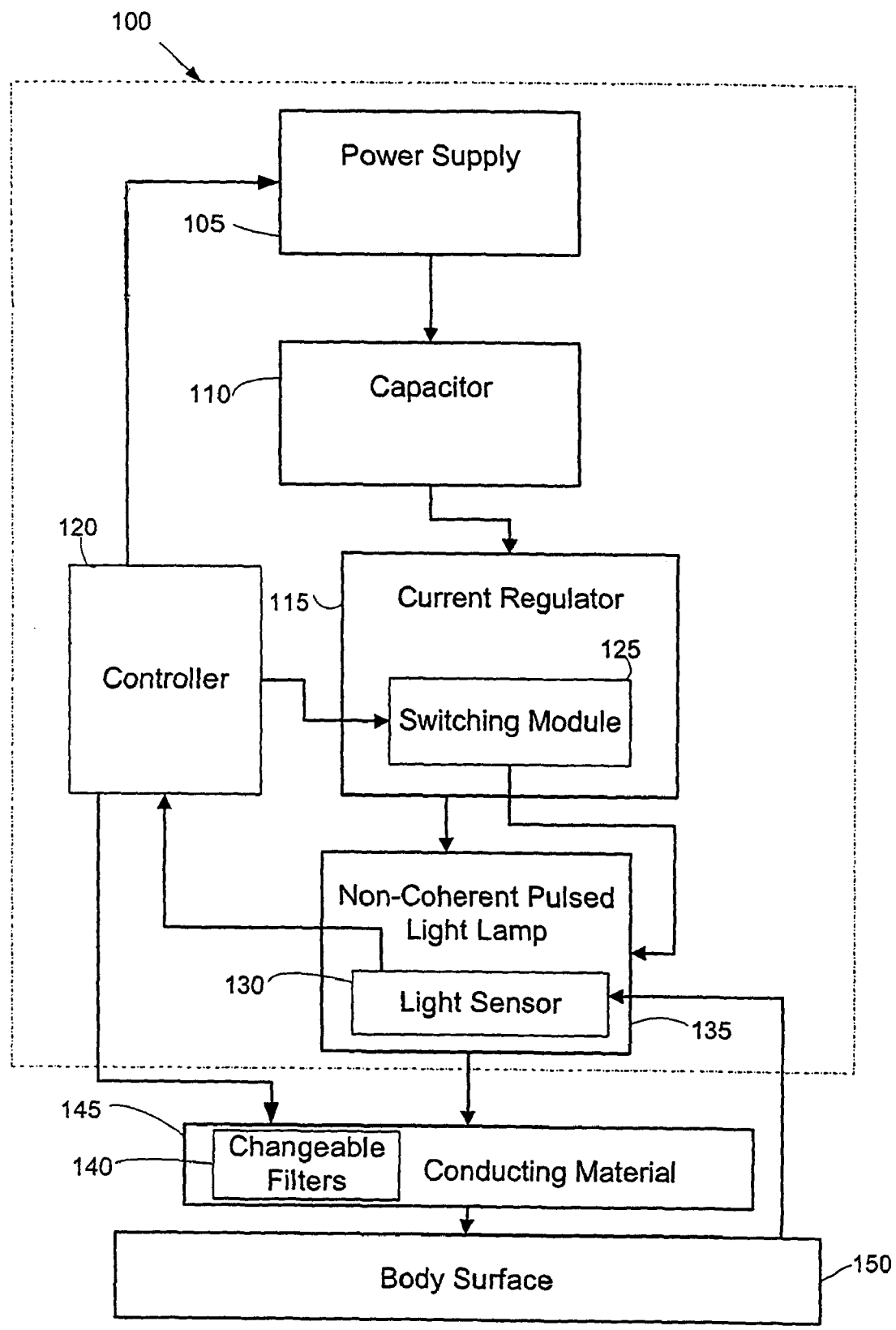
FIGS. 1A and 1B are a schematic illustrations of components of a non-coherent pulsed light system, according to some embodiments of the present invention.

It will be appreciated that for simplicity and clarity of illustration, elements shown in the drawings have not necessarily been drawn to scale and are being provided as non-limiting examples. For example, the dimensions of some of the elements may be exaggerated relative to other elements for clarity. Further, where considered appropriate, reference numerals may be repeated among the drawings to indicate corresponding or analogous elements throughout the serial views.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

In the following detailed description, numerous specific details are set forth in order to provide a thorough understanding of the present invention. However, it will be understood by those skilled in the art that the present invention may be practiced without these specific details.

Embodiments of the present invention may provide systems and methods to enable controlling of non-coherent pulsed light emitted by a light source, such as a lamp, thereby modulating the temporal distribution of the light and/or the spectral distribution output by the lamp within a pulse of light. The controlled current may enable, for example, changing the shapes of light pulses emitted by the lamp, such as, for example, squaring or smoothing of sub-pulses of non-coherent pulsed light, equalizing the sub-pulses, and delivering the energy over an extended period of time, according to a selected pulse shape or sub-pulse related to target specifications. The current control may enable changing of a pulse spectrum, during a pulse, to comply with target specifications. These developments may enable administration of customizable non-coherent pulsed light treatments, enabling enhanced safety and efficacy of such treatments. Sub-pulses, as described herein, may relate to pulses and/or portions of pulses that may be initiated, generated, delivered etc., according to some embodiments of the present invention. Pulses, as described and/or as claimed herein, may relate to whole pulses, partial pulses, sub-pulses or other suitable portions of pulses. For example, the length of a pulse and/or the combined lengths of one or more sub-pulses within a pulse may be between 1 ms to several seconds.

Reference is now made to FIG. 1A, which is a schematic illustration of a system 100 enabled to control non-coherent pulsed light applications, such as, for example, Intensed Pulse Light™ (IPL™) based skin treatments. As can be seen in FIG. 1, system 100 may include a power supply 105, which may include, for example, an electric power source, e.g., a battery or any other suitable source of electric power. A current source, for example a capacitor 110, may be provided to store a charge, and may be subsequently periodically discharged to generate current, which may be used to operate a lamp 135 producing non-coherent light energy in a pulsed mode. Power supply 105 may be connected to lamp 135 directly or via a current regulator and/or modulator 115, as described below. Lamp 135 may be operated in a pulsed mode, and may provide, for example, non-coherent pulsed light to one or more targets. Lamp 135 may include, for example, a xenon, krypton or any other light source that may generate a wide wavelength spectrum of light energy output. For example, an exemplary lamp 135 may provide light energy with wavelengths ranging between 300-1100 nanometers. Lamp 135 may be associated with at least one light sensor unit 130, to sense, for example, light intensity and/or light wavelengths in a vicinity of lamp 135. Light sensor unit 130 may be independent of lamp 135, or integrated into lamp 135. In other embodiments light sensor unit 130 may sense, for example, light intensity and/or light wavelengths reflected from a treatment area, for example, a body surface.

Current regulator and/or modulator 115 may be used to modulate energy flow (e.g., electric pulses) between power supply 105 and lamp 135 and/or between capacitor 110 and lamp 135. Current regulator/modulator 115 may include a controller unit 120, and a switching module 125. Controller unit 120 may be independent of current regulator 115 (as shown in FIG. 1), and/or in other embodiments may be included within current regulator 115 or within other suitable system components. Switching module 125 may be adapted to modulate the power supply or current provided to lamp 135, to effect changes in spectral distribution and/or light intensity emitted from lamp 135. Controller unit 120 may include a data storage unit (not shown), which may store executable code, non-coherent pulsed light data, treatment data, user data, and/or other relevant data. For example, pulse parameters for a treatment (including shape, energy, spectrum during different portions of pulse, etc.) may be prepared, according to the resolution of optical parameters between a target and the surrounding tissue. Such parameters may be stored in controller unit 120. Controller 120 may translate the pulse parameters to system parameters, such as capacitor voltage, lamp current etc., possibly using suitable software.

Controller 120 may be adapted to process illumination data received from light sensor 130. Results of the processing of data from light sensor 130 by controller 120 may be used to instruct switching module 125 to activate lamp 135 with a controlled current pattern. For example, switching module 125 may provide an appropriate current pattern to generate a temporal distribution of light, and a selected wavelength spectrum of light energy during a pulse from lamp 135. Controller 120 may, for example, determine the wavelength spectrum to be generated, thereby enabling spectrum switching during a pulse and/or during a sub-pulse, as described below with reference to FIGS. 4A-4C. Switching module 125 may include a current control module, to control the magnitude of current supplied to lamp 135. Such current control may affect the spectrum emitted by lamp.

A light conducting material 145, such as a light guide, gel or any combination thereof, or any other suitable material, may be placed on a body surface 150, to enable energy emitted by lamp 135 to flow efficiently to body surface 150. In some embodiments, efficient energy flow may be achieved by connecting current regulator 115 or modulator 125 directly to power supply 105, e.g., not via capacitor 110. In some embodiments, efficient energy flow and/or control over current delivered to lamp 135 may be achieved by using filters, for example, changeable or variable filters 140. Filters 140, however, may be changed according to a pre-determined plan, without feedback. According to one embodiment of the present invention, results of the processing of data from light sensor 130 by controller 120 may be used to control operation of filters, for example, to change pulse wavelengths within a pulse. Filters 140 may include, for example, cut on filters, cut off filters, band pass filters, neutral density filters, and/or any other suitable filters having one or more different light spectrum and/or light intensity capabilities.

Figure 1B:
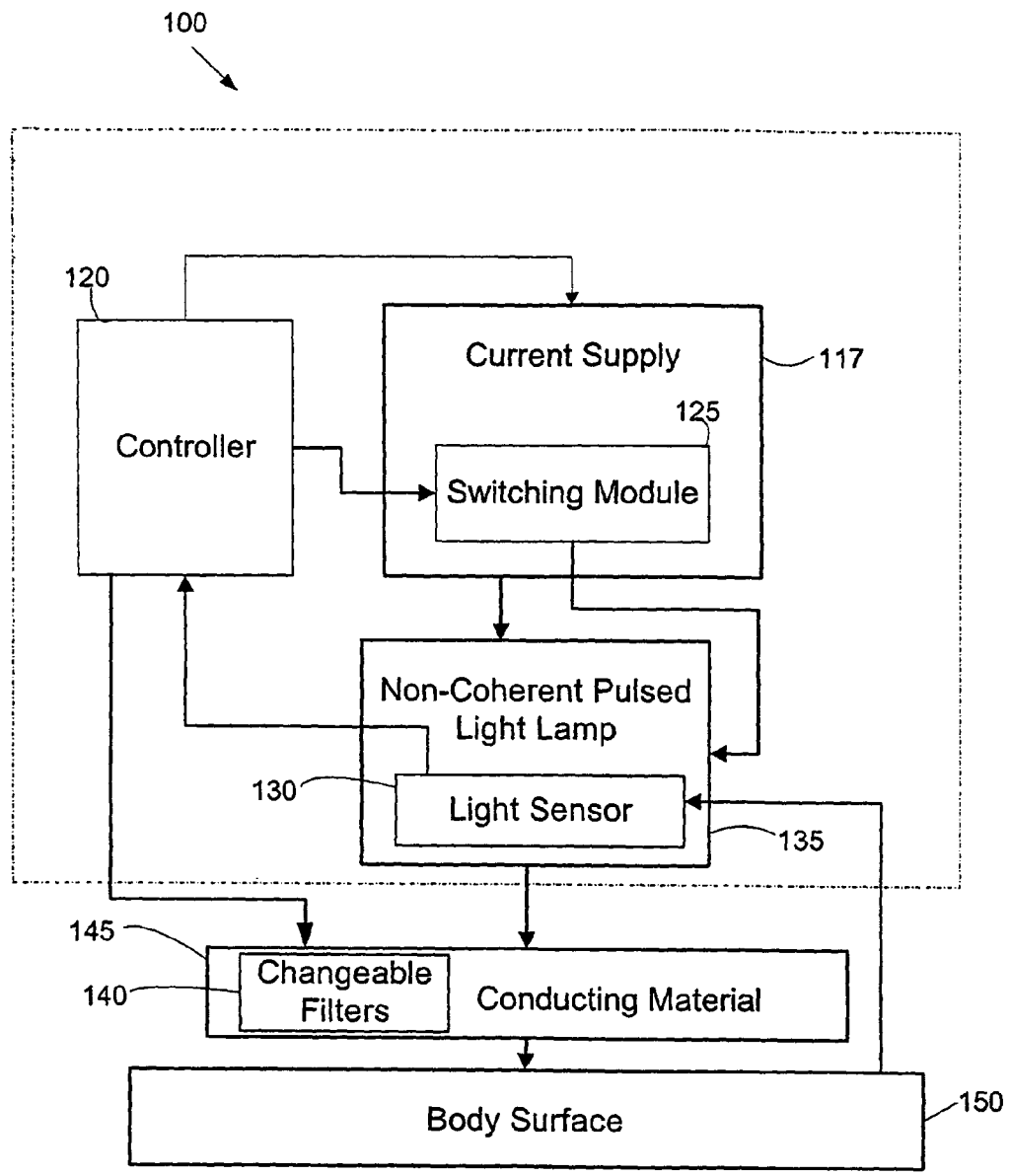

In other embodiments, as can be seen with reference to FIG. 1B, system 100 may be provided with energy by a current supply 117, which may supply current at selected durations, intensities, or other selected criteria.

Figure 2:
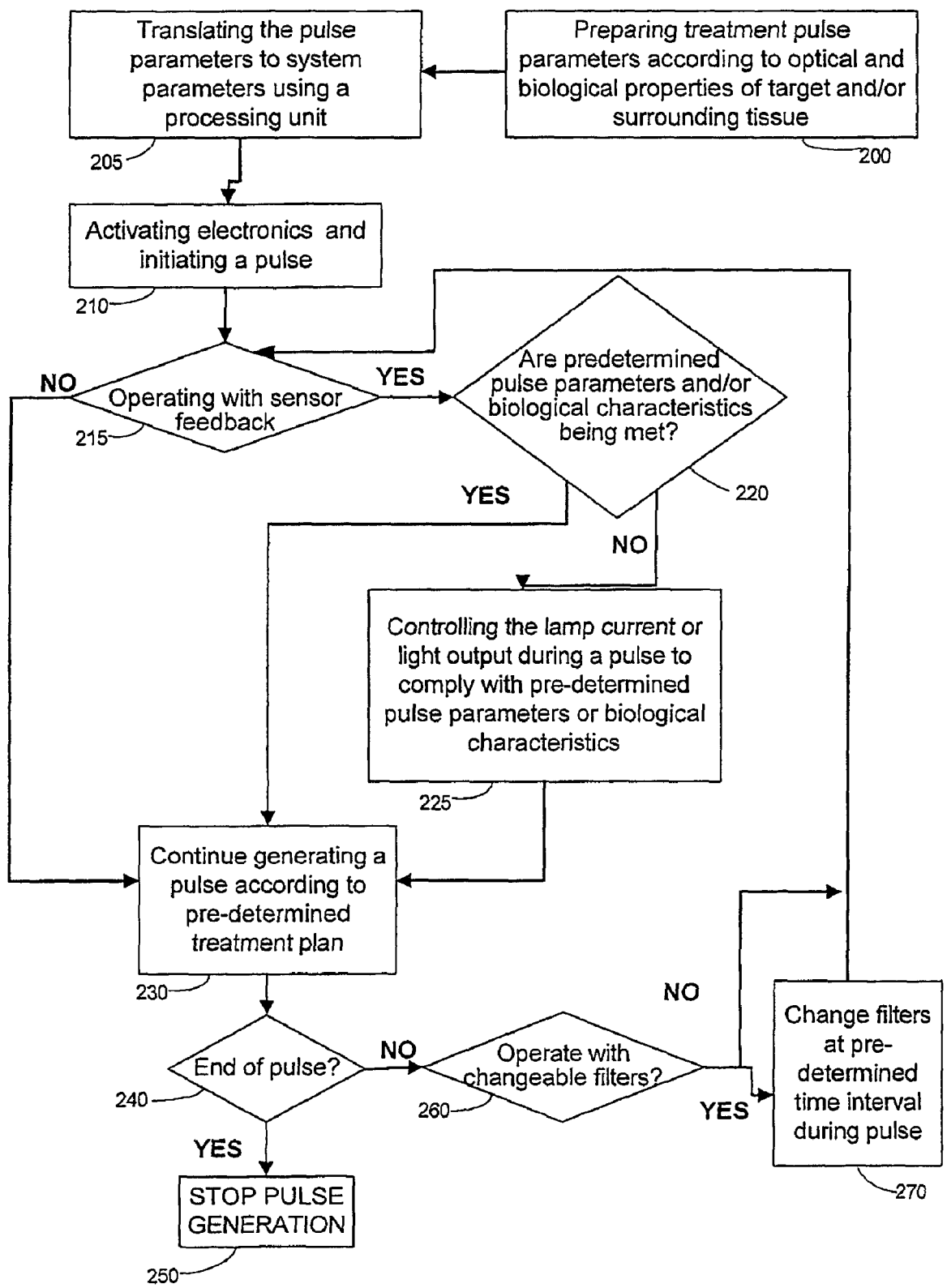
FIG. 2 is a flow chart illustrating a method of controlling non-coherent pulsed light output according to some embodiments of the present invention.

FIG. 2 schematically illustrates a method of controlling non-coherent pulsed light. As can be seen in FIG. 2, at block 200 a treatment plan may be prepared, for example, using a processing unit associated with treatment software. For example, treatment software may enable preparation of treatment pulse parameters, such as shape, energy, and spectrum etc., during the different portions of a pulse and/or a sub-pulse, according to optical and/or biological properties of a target and/or of surrounding tissue. At block 205 the pre-defined pulse parameters may be translated into system parameters, such as capacitor voltage, lamp current etc., for example by a processing unit associated with treatment software. At block 210 a pulse may be initiated, for example, using a power supply to a charge capacitor to generate one or more pulses, to activate a lamp. Current may be supplied directly to the lamp from the power supply, for example, not via the capacitor. At block 215 system 100 may determine whether or not to operate with sensor feedback, for example using a controller.

Pulse(s) may be operated in a plurality of modes, or in any combination of modes. In a first mode, indicated by block 220, the method may be implemented using sensor feedback ("YES" at block 215). The light output that may be sensed by a sensor, for example, a light sensor, may be received and processed by the controller. The light sensor may sense parameters such as light intensity, light wavelengths etc. Other sensors, for example current sensors or tissue temperature sensors etc. may also be used. At block 220, the controller may process signals from the sensor, to determine if the light output complies with predetermined pulse parameters and/or biological characteristics. At block 220, if the predetermined pulse parameters are being met ("YES" at block 220), a current regulator may enable a continued generation of pulses and/or sub-pulses according to the initial predetermined treatment pulse parameters, at block 230. At block 225, if the predetermined pulse parameters are not being met ("NO" at block 220), the controller may control the lamp current and/or light output, thereby determining the lamp output during a pulse. In this way, the adjusting of electrical input parameters may enable compliance of a pulse and/or a sub-pulse to predetermined pulse parameters and/or biological characteristics. For example, a switching module may increase or decrease the current to the lamp, optionally during a pulse, to increase, decrease, or maintain the light output from the lamp at selected levels. For example, changing the current during a pulse and/or during a sub-pulse may enable spectrum shifting of light emitted by the lamp during a pulse and/or during a sub-pulse, and/or changing of temporal distribution of light emitted by the lamp during a pulse and/or during a sub-pulse.

In a second mode, indicated by block 230, the method may be implemented without using sensor feedback ("NO" at block 215), according to the predetermined treatment plan. At block 240, the controller may determine whether or not to end the pulse. At block 250, if the controller determines to end the pulse ("YES" at block 240), pulse generation may be stopped. At block 260, if the controller determines to continue the pulse ("NO" at block 240), controller may determine whether or not future portions of a pulse require changing of filters. At block 270, if the controller determines to operate with changeable filters ("YES" at block 260), filters may be changed at predetermined time intervals during a pulse. At block 270, the method may continue from block 215, where a decision whether to operate a subsequent pulse portion with or without feedback may be determined. At block 260, if the controller determines to operate without changeable filters ("NO" at block 260), the method may continue from block 215, where a decision whether to operate a subsequent pulse portion with or without feedback may be determined. For example, a spectral filter, such as a cut on, cut off, band pass or other filter, may be used with the lamp at a constant current. For example, a neutral density filter may be used to control the temporal shape of the pulse and/or a sub-pulse, during the pulse, without making spectral changes. Any combination of some or all of the above functions, as well as additional suitable functions, may be implemented.

In this way, the pulse shape representing the light output from the lamp may be controlled to comply with target specifications. For example, if the light intensity is too high, or the spectrum being illuminated by the lamp is out of the required spectrum limits for a target being treated, the regulator may control the energy supplied to the lamp during a pulse to generate the required light output, for example, according to a selected spectrum, a selected pulse length, and/or a duty cycle. Carefully tuned pulses and/or sub-pulses may produce considerable temperature rises at the target, while maintaining temperatures in adjacent tissues well below a selected safety threshold. For example, changing the spectral distribution may enable outputting a significant quantity of light energy in a yellow light range, for example, by increasing the current. In addition, for example, the current may be lowered and a short (e.g. 500 nm) cut-off filter may be used, thereby maintaining most of the light in the safer IR region of the spectrum. Later during the pulse, the current may be increased to enable shifting of the spectrum towards the yellow visible light range.

According to an embodiment of the present invention, target tissue parameters may be measured during a pulse, and pulses or sub-pulses may be adjusted during the pulse to optimize the treatment. Both spectrum distribution and time dependence of pulse amplitudes may be varied according to the type, position, and dimensions of a selected target, or modifications of target parameters during treatment. Such operations may enable optimal light energy to be applied to selected targets, providing relatively efficient and safe usage of light energy to treat target locations.

According to some embodiments of the present invention, at least one physical property may be defined that differentiates between one or more targets and surrounding tissue, to enable increasing the targeted effect of treatment, while preserving the surrounding tissue. For example, altering the resolution of optical parameters between a target and the surrounding tissue may enable differentiation of targets located in dark skin types, targets having physical properties similar to or only slightly different from—surrounding tissue, targets located deep in the dermis, and/or combinations of the above. Such differentiation may enable, for example, increased safety and/or efficacy when applying treatments including hair removal, blood vessel treatments, textural lesion treatments etc.

Reference is now made to FIGS. 3A-3E, which schematically illustrate light energy outputs, according to some embodiments of the present invention. As can be seen with reference to FIG. 3A, traditional non-coherent pulsed light pulse shapes or sub-pulse shapes, such as pulses 31 and 32, may be characterized by an energy peak at the beginning of the pulse, or sub-pulse, followed by a rapid decline in the energy delivered to a target. Such energy output patterns may generally result from insufficient control of the discharge from a capacitor 110. Energy supplied above an optimal level 33, represented by area 34, may be, for example, dangerous and/or unusable energy. Energy levels below optimal level 33, represented by area 35, may relate to energy deficiencies as a result of outputs from a capacitor that are too low to impact effectively on a target.

Figure 3A:
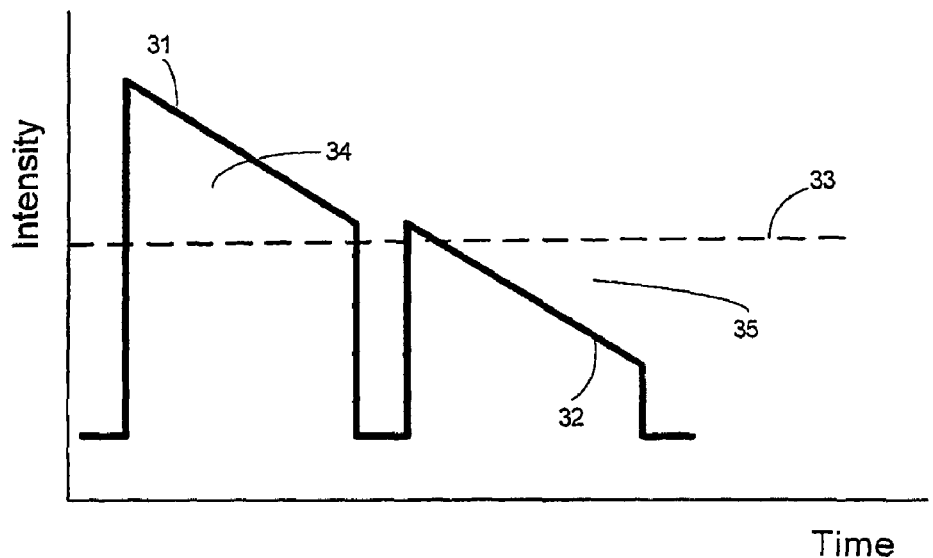
FIGS. 3A-3E are graphical illustrations of light output as a function of time, according to some embodiments of the present invention.
Figure 3B:
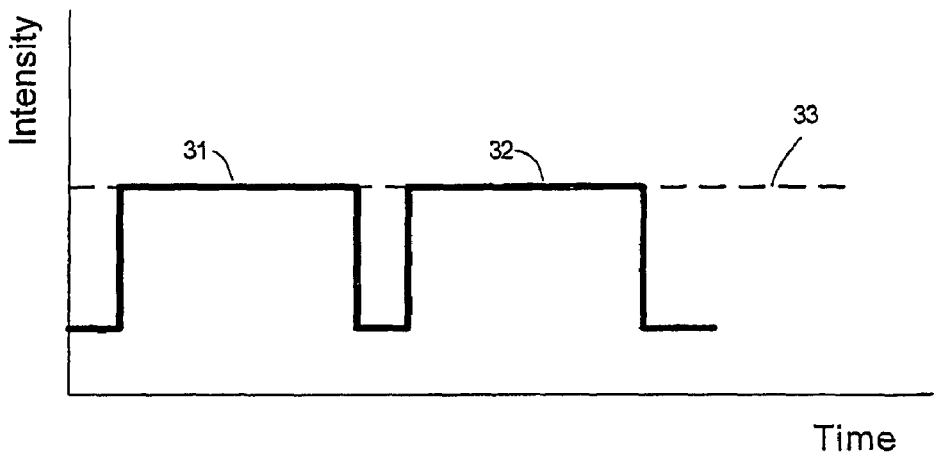
Figure 3C:
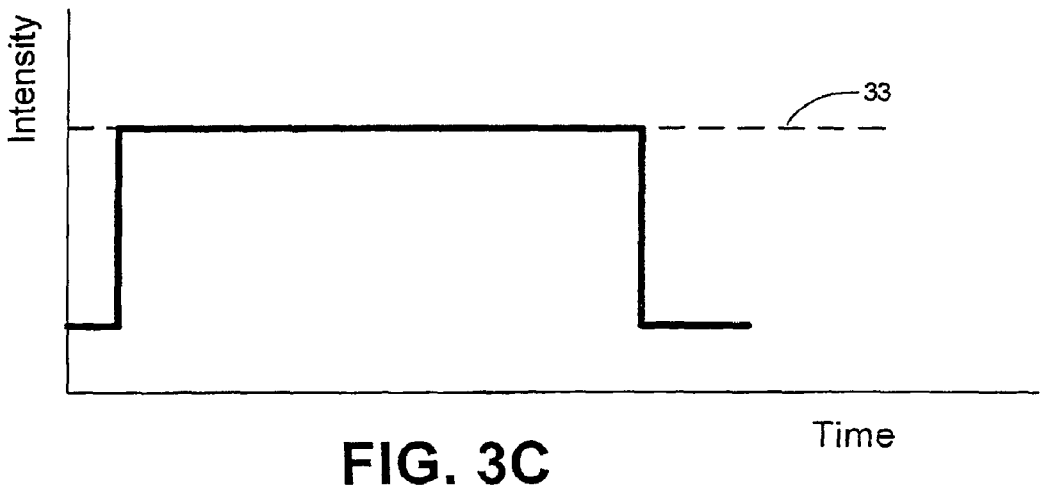

FIGS. 3B-3E, for example, illustrate various examples of pulse shapes that may be provided by a light source producing non-coherent pulsed light, such as lamp 135, according to some embodiments of the present invention. As described above, controller 120, in association with capacitor 110, current regulator 115, and/or switching module 125 may provide pulses of energy that may be controlled, for example to produce pulses and/or sub-pulses of selected durations, intensities etc. In FIG. 3B, for example, the sub-pulses 31, 32 have been squared or smoothed to optimal level 33, according to selected values, thereby equalizing the energy emitted by the sub-pulses. FIG. 3C illustrates an example of an extended pulse, which may be a relatively long and relatively low power pulse. For example, relatively long square pulses may enable lamp 135 to operate at a low current (e.g., with a low plasma temperature), which may lead to spectral distribution with, for example, a maximum wavelength of between 800 and 1000 nm. Such a shift of the non-coherent pulsed light output may be used to provide relatively high safety levels for non-coherent pulsed light treatments. For example, treatments for darker skinned people may require relatively longer exposure, by giving fluence over an extended period of time. Such a system may therefore enable relatively safer treatment of dark skinned people, though possibly at a lower efficacy yield. As can be seen in FIGS. 3B-3C, electric energy supplied to the lamp may be controlled to provide a selected light intensity, represented by line 33.

Figure 3D:
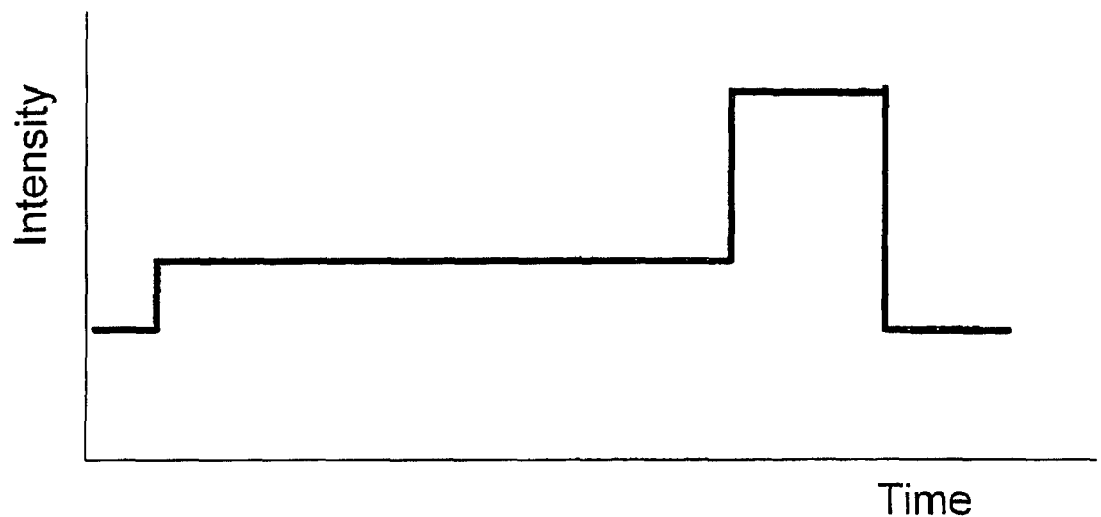

According to some embodiments of the present invention, a multiple stage non-coherent pulsed light treatment may be provided. For example, a light output from a lamp may be used to enable pre-heating of a target. The light output, for example, according to the pulse length or spectrum, may be adapted to enable implementation of a selected treatment at the target. Examples of multi-stage treatments may be seen with reference to FIGS. 3D-3E. FIG. 3D illustrates an example of a relatively long, low power, pre-heating IR shifted pulse followed by a high impact pulse (e.g., towards green/yellow wave length).

Figure 3E:
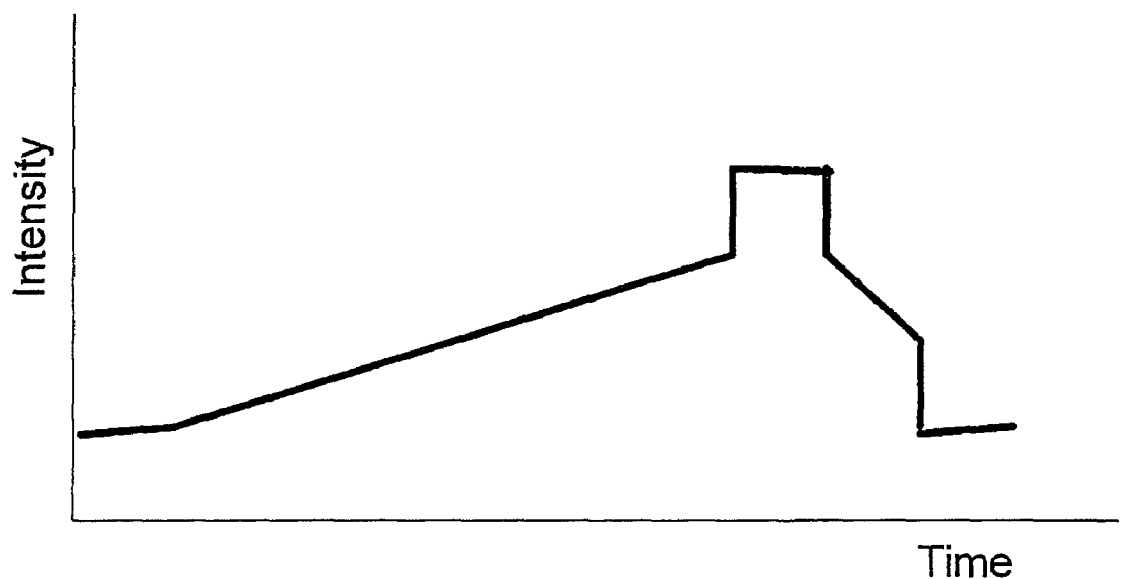

FIG. 3E illustrates an exemplary customized controlled pulse. Such a pulse, as can be seen in FIG. 3E, may provide improved safety and efficiency, as it may be tailored or customized according to target and skin type, or any other factors. For example, a non-specific heating of tissue, from the deeper to the more superficial zones, together with a chilling procedure that may further cool the epidermis during the non-coherent pulsed light procedure, may be administered. Of course, other pulse types and dimensions may be used. Any number of stages, or combinations of stages, may be used.

In some embodiments the preheating pulse may be, for example, be used to implement non-specific heating of one or more targets and surrounding tissue. Preheating may utilize, for example, pulses in the red-infrared range. A subsequent treatment pulse or sub-pulse may be utilized. Such a treatment pulse may be, for example, in the yellow-blue spectrum range (e.g., 400-600 nm). Other suitable ranges may be used.

In the case of treatments using changes in spectral distribution, the length of the pulse or of the total sub-pulses may be, for example, between 1 ms up to 1 sec. The change of the related spectral distribution may be, for example, between 300 and 1,500 nm. The controlled change of spectral distribution may be implemented by precisely controlling the current provided to the lamp, and/or by using flying or changing filters.

In the case of treatments using changes in light intensities, the length of the pulse or of the total sub-pulses may be, for example, between 1 ms up to 1 sec. The current provided to the lamp may be, for example, between 10 and 600 Amps. In some embodiments the current density may be, for example, between 100-4000 Amps/cm2, or the plasma temperature may be, for example, between 1,000 to 12,000K.

According to some embodiments of the present invention, treatments with multiple modes of operation within a pulse may enable differentiation between one or more targets and surrounding tissue. Such treatments may help improve the safety and/or efficacy of treatments of targets located in dark skin types, of targets having physical properties similar to or only slightly different from surrounding tissue, of targets located deep in the dermis, and/or any combinations of the above treatments. Furthermore, treatment for hair removal, blood vessel modification, textural lesions and/or other procedures may be aided using treatments with multiple modes of operation within a pulse, as described above.

Figure 4A:
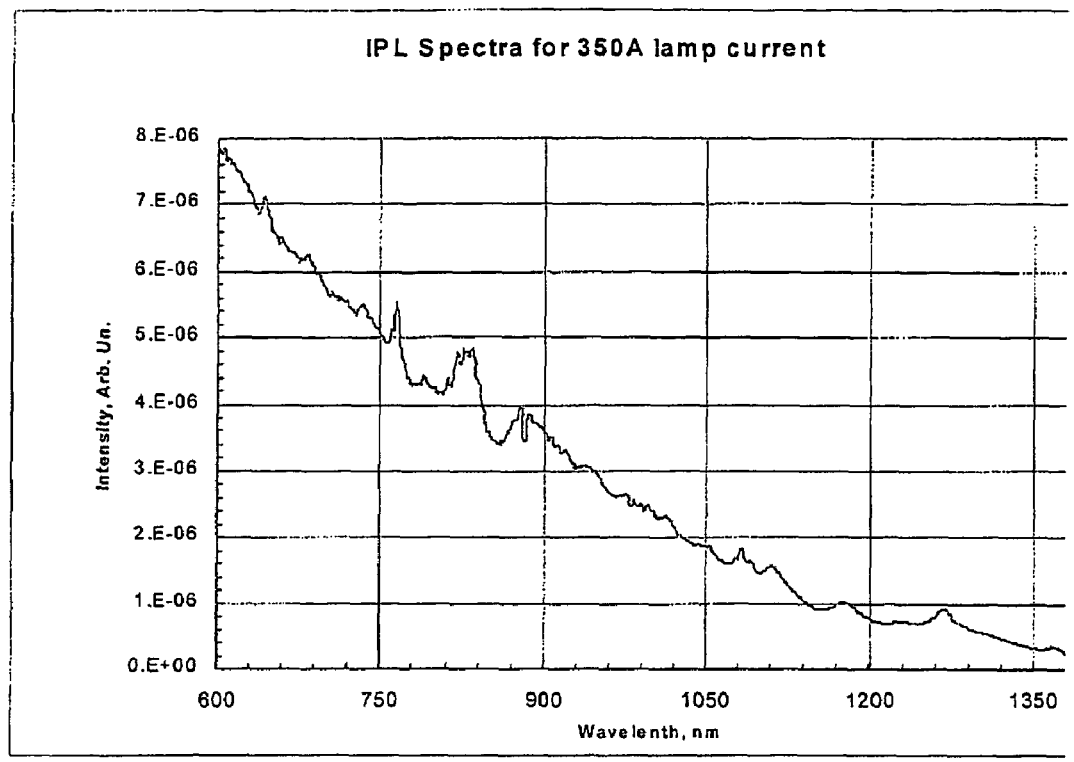
FIGS. 4A-4C are examples of measured spectra of light output of, for example, a xenon lamp, as a function of energy input according to some embodiments of the present invention.
Figure 4B:
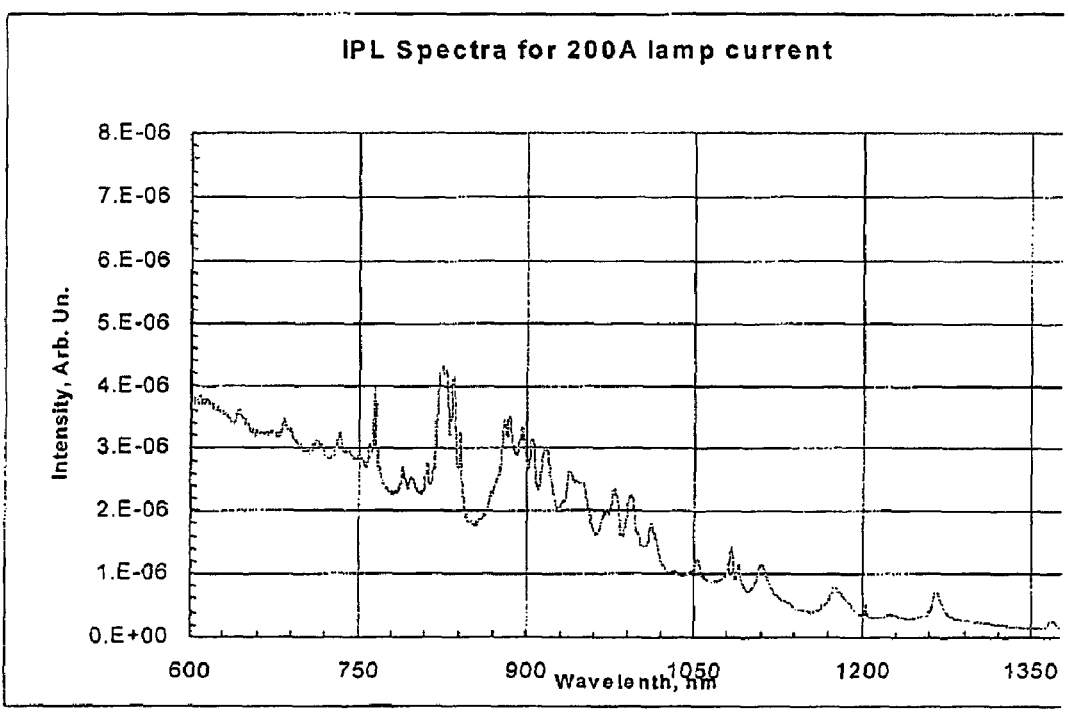
Figure 4C:
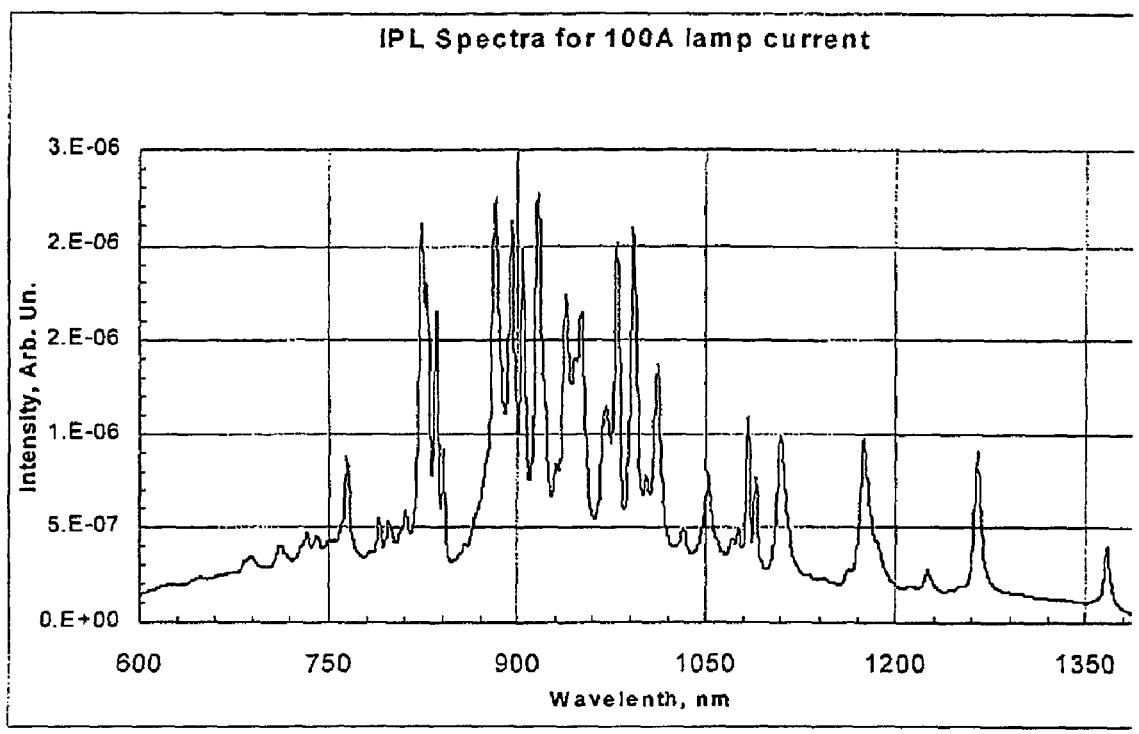

Reference is now made to FIGS. 4A-4C, which are graphs illustrating examples of spectral distribution of light output from a light source producing non-coherent pulsed light, such as lamp 135, for different current input (in Amperes), for example, delivered from power supply 105 or capacitor 110 to lamp 135. As can be seen in FIG. 4A, when providing a pulse of 350 Amperes (A), for example, the resulting output from lamp 135 may provide a certain spectrum and light intensity. When providing a pulse of 200 A, for example, as can be seen in FIG. 4B, the resulting output from lamp 135 may provide a shift in spectrum and light intensity. When providing a pulse of 100 A, for example, as can be seen in FIG. 4C, the resulting output from lamp 135 may provide further shift of the spectrum and light intensity. Generally, FIGS. 4A-4C show a shift in the spectrum towards the infrared wavelengths, resulting from the change (reduction) of current supplied to the lamp and/or the change of intensity. These phenomena may be formed during pulses, using methods and devices of the present invention.

According to some embodiments of the present invention, regulator 125 may enable modulation of the output to lamp 135, such that a selected output may be provided to lamp 135. This selected output, according to an embodiment of the present invention, may be, for example, a suitable mixture or combination of the current inputs described with reference to FIGS. 4A-4C, or other current inputs. A controlled current input as described above may enable emission of light energy according to the requirements of one or more selected targets. For example, the output may be controlled to yield a relatively constant light intensity, a predetermined spectrum, selected pulse duration or sub-pulse duration, a desired duty cycle, a combination of pulses, and/or other selected pulse parameters. The ability to change a spectrum of outputted light energy may be referred to as spectrum switching, which, according to some embodiments of the present invention, may be implemented within a pulse.

According to some embodiments of the present invention, two-part pulses, for example, may be used to control light output for a given treatment, for example, for wrinkle reduction. For example, in a first operation a low power, long duration, pulse may be generated for preheating at a low plasma temperature (e.g. using light in the infrared spectrum). During this operation the tissue may be heated to just below a damage threshold, for example, in a non-selective way, to a depth of up to approximately 2 mm. Simultaneously, cooling, for example contact cooling, may be applied to decrease the temperature of a treatment area, for example the epidermis. In a second stage, a relatively short, higher power, pulse may be generated. The plasma temperature during the second stage may be chosen, for example, to match the absorption of hemoglobin. In such a case, the temperature around small capillaries may increase to a level, where, for example, collagen re-generation may occur, which may lead to skin rejuvenation.

According to some embodiments of the present invention, two-part or multi-part pulses, as described above, may be used to control light output for, for example, effective treatment of medium size blood vessels. For example, a first sub-pulse may be generated with high power for a short duration, with most of the light in the green-yellow spectral region. This sub-pulse may initiate, for example, a red shift of blood absorption. A second sub-pulse that is tuned to emit infrared light may be generated, which may be less dangerous to the epidermis.

According to some embodiments of the present invention, mechanical filters may be changed during a pulse, in addition to current change, or in any combination. The usage of filters may refer to changeable filters, flying filters, or other suitable filters that may have different light spectrum filtering characteristics and/or different light intensifying characteristics, to enable control of non-coherent pulsed light during a pulse. The mechanism for controlling the changeable filters may be similar to a mechanical camera shutter. Such filters may be used with or without a switching module 125 to change the pulse shape emitted from lamp 135, during a pulse. For example, a spectral filter, such as a cut on, cut off, band pass or other filter, may be used with lamp 135 operated at a constant current, to change the spectrum emitted during a pulse. For example, a neutral density filter may be used to control the temporal shape of the pulse without making spectral changes.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A system to provide non-coherent pulsed light, the system comprising:
   a lamp to produce non-coherent pulsed light;
   a current supply to controllably provide current to said lamp and to enable controlled spectral distribution and controlled temporal intensity distribution of said non-coherent pulsed light within a pulse of said non-coherent light, the controlled spectral distribution and the controlled temporal intensity distribution of said non-coherent pulsed light being controlled, at least in part, by altering the current from the current supply to cause altering the spectral distribution and the temporal intensity distribution during the pulse;
   one or more changeable filters to enable separate controlled altering of the spectral distribution and the temporal intensity distribution of said non-coherent pulsed light during the pulse;
   a feedback mechanism configured to:
      perform a determination if output resulting from application of said pulse of non-coherent light on a target area is in accordance with a treatment plan, and
      change the treatment plan to perform, based, at least in part, on the determination of the feedback mechanism, one or more of: altering the current from the current supply to alter the spectral distribution and the temporal intensity distribution of said non-coherent pulse light during the pulse, and controlling the one or more changeable filters; and
   a controller unit to control at least one of the current supply, the one or more changeable filters and the feedback mechanism, the controller unit configured to enable control one or more of the spectral and the temporal intensity distribution of said non-coherent pulsed light for the selected treatment, based, at least in part, on data received from said feedback mechanism.

2. The system of claim 1, wherein said current supply is configured to initiate the pulse having an initial spectral distribution based on the treatment plan before any changing of the treatment plan.

3. The system of claim 1, wherein said current supply is configured to substantially maintain a selected level of said spectral distribution during the pulse of non-coherent light.

4. The system of claim 1, wherein said controller is associated with treatment software.

5. The system of claim 1, wherein said current supply is configured to initiate the pulse having an initial temporal intensity distribution based on the treatment plan before any changing of the treatment plan.

6. The system of claim 1, wherein said current supply is configured to substantially maintain a selected level of said temporal intensity distribution during the pulse of non-coherent light.

7. The system of claim 1, wherein the feedback mechanism comprises:
   a light sensor to:
      sense the non-coherent pulsed light produced by the lamp,
      generate signals based on the sensed non-coherent pulsed light, and
      provide the generated signals to the feedback mechanism.

8. The system of claim 1, wherein the changeable filters are configured to be changed at predetermined time intervals during the pulse.

* * * * *